United States Patent
Constantine et al.

(10) Patent No.: US 10,111,826 B2
(45) Date of Patent: *Oct. 30, 2018

(54) SOLID COSMETIC COMPOSITION HAVING DISPERSED THEREIN GAS BUBBLES, AND A PROCESS FOR MAKING A SOLID COSMETIC COMPOSITION

(71) Applicant: Cosmetic Warriors Limited, Poole, Dorset (GB)

(72) Inventors: Mark Constantine, Dorset (GB); Margaret Joan Constantine, Dorset (GB); Helen Elizabeth Ambrosen, Dorset (GB)

(73) Assignee: COSMETIC WARRIORS LIMITED, Poole, Dorset (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/650,828

(22) PCT Filed: Nov. 26, 2013

(86) PCT No.: PCT/GB2013/053113
§ 371 (c)(1),
(2) Date: Jun. 9, 2015

(87) PCT Pub. No.: WO2014/091196
PCT Pub. Date: Jun. 19, 2014

(65) Prior Publication Data
US 2016/0193137 A1    Jul. 7, 2016

(30) Foreign Application Priority Data
Dec. 11, 2012 (GB) .................................. 1222275.8

(51) Int. Cl.
*A61K 8/92* (2006.01)
*A61Q 19/00* (2006.01)
*A61K 8/04* (2006.01)

(52) U.S. Cl.
CPC .............. *A61K 8/922* (2013.01); *A61K 8/046* (2013.01); *A61Q 19/00* (2013.01); *A61K 2800/5922* (2013.01)

(58) Field of Classification Search
CPC .............. A61K 8/92; A61K 8/02; A61Q 19/00
See application file for complete search history.

(56) References Cited

U.S. PATENT DOCUMENTS

| | | | |
|---|---|---|---|
| 4,195,935 A | 4/1980 | Sollich | |
| 4,889,738 A | 12/1989 | Hara | |
| 4,919,964 A * | 4/1990 | Adams | A23D 7/011 426/564 |
| 5,370,888 A | 12/1994 | Hachiya et al. | |
| 2001/0014315 A1 | 8/2001 | Harbeck | |
| 2003/0007943 A1 | 1/2003 | Krause et al. | |
| 2003/0157050 A1 | 8/2003 | Ambrosen et al. | |
| 2004/0247531 A1 | 12/2004 | Riedel et al. | |
| 2005/0282717 A1 | 12/2005 | Volz et al. | |
| 2006/0147390 A1 | 7/2006 | Schreiber et al. | |
| 2006/0270743 A1 | 11/2006 | Rossow | |
| 2006/0292193 A1 | 12/2006 | Lee et al. | |
| 2007/0166253 A1 | 7/2007 | Kostick et al. | |
| 2007/0196298 A1 | 8/2007 | Kostick et al. | |
| 2008/0089916 A1 | 4/2008 | Magee et al. | |
| 2008/0193622 A1 | 8/2008 | Haedelt et al. | |
| 2009/0208438 A1 | 8/2009 | Gorman | |
| 2009/0312213 A1 | 12/2009 | Tanaka et al. | |
| 2010/0189662 A1 | 7/2010 | Neuboug | |
| 2011/0030714 A1 | 2/2011 | Iijima | |
| 2012/0107256 A1 | 5/2012 | Delvalle et al. | |
| 2012/0276030 A1 * | 11/2012 | Marthaler | A61Q 1/02 424/63 |
| 2016/0193137 A1 | 7/2016 | Constantine et al. | |

FOREIGN PATENT DOCUMENTS

| | | |
|---|---|---|
| CN | 1043607 A | 7/1990 |
| CN | 101208013 A | 6/2008 |
| DE | 102005011459 A1 | 9/2006 |
| DE | 102006051682 A | 2/2008 |
| DE | 102006051685 A1 | 5/2008 |
| EP | 0375238 A2 | 6/1990 |
| EP | 2 052 628 | 4/2009 |
| FR | 2 614 313 | 10/1988 |
| FR | 2949972 A1 | 3/2011 |
| GB | 459583 A | 1/1937 |
| GB | 2 361 641 | 10/2001 |
| GB | 2 492 138 | 12/2012 |
| JP | S62-275648 A | 11/1987 |
| JP | H04-234948 A | 8/1992 |
| JP | 2001-199877 A | 7/2001 |
| JP | 2002-145720 A | 5/2002 |
| JP | 2003-095917 A | 4/2003 |
| JP | 2003-531846 A | 10/2003 |
| JP | 2004-256805 A | 9/2004 |
| JP | 3636314 B | 4/2005 |
| JP | 2007-501835 A | 2/2007 |
| JP | 2007-169230 A | 7/2007 |
| JP | 2007-197401 A | 8/2007 |
| JP | 2008-024636 A | 2/2008 |
| JP | 2008-247882 A | 10/2008 |
| JP | 2008-539774 A | 11/2008 |
| JP | 2009-040818 A | 2/2009 |
| JP | 2009-508836 A | 3/2009 |
| JP | 2010-506834 A | 3/2010 |
| JP | 2010-168296 A | 8/2010 |
| JP | 2010-530400 A | 9/2010 |
| JP | 4559194 B2 | 10/2010 |
| JP | 2012-531395 A | 12/2012 |
| KR | 20110057815 A | 6/2011 |

(Continued)

OTHER PUBLICATIONS

Arnold (Everybody Loves Ice Cream 2004 pp. 22, 23, 52 and 54).*

(Continued)

*Primary Examiner* — Ernst V Arnold
(74) *Attorney, Agent, or Firm* — Merchant & Gould P.C.

(57) ABSTRACT

A solid cosmetic composition includes a vegetable butter. Gas bubbles are dispersed in the solid cosmetic composition. The gas bubbles form from 5 to 19% of the volume of the solid cosmetic composition.

17 Claims, No Drawings

(56) References Cited

FOREIGN PATENT DOCUMENTS

| | | |
|---|---|---|
| RU | 2156614 C1 | 9/2000 |
| RU | 2240106 C1 | 11/2004 |
| RU | 2376346 C2 | 12/2009 |
| WO | 00/57715 A1 | 10/2000 |
| WO | 01/15543 A1 | 3/2001 |
| WO | 2004/056191 A1 | 7/2004 |
| WO | WO 2004/087856 | 10/2004 |
| WO | 2005/002352 A1 | 1/2005 |
| WO | 2005/006870 A1 | 1/2005 |
| WO | 2006/094567 A1 | 9/2006 |
| WO | 2006/122823 A1 | 11/2006 |
| WO | WO-2006122823 A1 * 11/2006 | ............ A23G 1/00 |
| WO | 2007/031793 A2 | 3/2007 |
| WO | 2009/142275 A1 | 11/2009 |
| WO | WO 2012/149436 | 11/2012 |

OTHER PUBLICATIONS

Clarke (The Science of Ice Cream 2012 Royal Society of Chemistry pp. 62, 65, 106).*

Oils-Melting Points [online] retrieved on Oct. 27, 2016 from: http://www.engineeringtoolbox.com/oil-melting-points-d_1088.html 1 page.*

The Quartermaster Corps: Organization, supply and services, 1953, p. 179; 1 page.*

The Billboard, Vendoer to get new chocolate bar after war that won't melt, 1944, p. 62; 1 page.*

International Preliminary Report on Patentability and Written Opinion; PCT/GB2013/053113, dated Jun. 16, 2015 (9 pages).

Edited by Y.H. Hui: Industrial and Consumer Nonedible Products from Oils and Fats; Bailey's Industrial Oil and Fat Products, Fifth Edition, vol. 5 (2001), 7 pages.

Office Action issued in corresponding Chinese Patent Application No. 2013800649063, dated Nov. 3, 2016.

Examination Report for British Patent Application No. 1222275.8, dated May 2, 2017.

Office Action issued in corresponding Russian Patent Application No. 2015 127 900, dated Apr. 13, 2017.

Search Report issued in corresponding Japanese Patent Application No. 2015-546087, dated Jul. 19, 2017.

International Search report and Written Opinion for International Application No. PCT/GB2013/053113 dated Nov. 17, 2014 (17 pages).

"How to Make Body Butter Q and A—Aromatherapy Recipes—How to Make Body Butter." http://wayback.archive.org/web/20100715072728/http://www.easy-aromatherapy-recipes—retrieved Nov. 8, 2013 (2 pages).

"Citrus Mango Body Butter Recipe—Aromatherapy Recipes." http://web.archive.org/web/20100717064412/http://www.easy-aromatherapy-recipes.com retrieved Nov. 26, 2014 (4 pages).

Campos et al. "Molecular Composition Dynamics and Structure of Cocoa Butter." *Crystal Growth & Design Article*. vol. 10. (2010) pp. 205-217.

"Lavender Oil", MedlinePlus Medical Encyclopedia, U.S. National Library of Medicine, National Institute of Health, http://www.nlm.nih.gov/medlineplus/ency/article/002711.htm (retrieved Feb. 24, 2015).

Notice of Decision to Grant for Japanese Patent Application No. 2014-516442, dated Sep. 1, 2016.

Notice of Decision to Grant for Russian Patent Application No. 2014101928/15, dated Mar. 18, 2016.

Unknown. "Chocolate-based cosmetics pamper sense more than skin." The Hindu. (Nov. 15, 2011) http://www.thehindu.com/sci-tech/health/medicine-and-research/chocolatebased-cosmetics-pamper-sense-morethan-skin/article1540660.ece.

International Search report and Written Opinion for International Application No. PCT/GB2012/051440 dated Dec. 18, 2013.

Haedelt et al. "Vacuum-induced Bubble Formation in Liquid-tempered Chocolate." J. of Food Science. vol. 70., No. 2, 2005: E159-E162.

Unknown. "Aromatherapy Recipes: How to Make body butter." http://wayback.archive.org/web/20100715072728/http://www.easy-aromatherapy-recipes.com/body-butterrecipe.html Jul. 15, 2010.

Unknown. "Aromatherapy Recipes: Citrus Mango Body Butter Recipe" http://wayback.archive.org/web/20100715072728/http://www.easy-armatherapy-recipes.com/body-butterrecipe.html Jul. 17, 2010.

Mintel, GNPD Databank "100% Natural Shea Butter", accession No. 1437736, Oct. 2010.

Mintel GNPD Databank "Pure Cocoa Butter" accession No. 1434344, Nov. 2010.

Andreas Domsch, "Cosmetic Preparations", vol. III, Lipid-Containing and Emulsified Formulations 4th Edition of the Work established by G.A. Nowak:20-21 (1994).

Wikipedia entry, "Kakaobuttter", downloaded May 24, 2017.

Mintel GNPD Databank "Whipped Shea Butter" accession No. 1877306, Sep. 2012.

Mintel GNPD Databank "Cocoa Butter Bath Bon Bons", accession No. 1042600, Feb. 2009.

Office Action for Korean Patent Application No. 10-2014-7001844, dated Aug. 3, 2018.

Joey Green "Clean It! Fix It! Eat It!" 1 page (2001).

\* cited by examiner

SOLID COSMETIC COMPOSITION HAVING DISPERSED THEREIN GAS BUBBLES, AND A PROCESS FOR MAKING A SOLID COSMETIC COMPOSITION

This application is a National Stage Application of PCT/GB2013/053113, filed 26 Nov. 2013, which claims benefit of Serial No. 1222275.8, filed 11 Dec. 2012 in Great Britain and which applications are incorporated herein by reference. To the extent appropriate, a claim of priority is made to each of the above disclosed applications.

FIELD OF THE INVENTION

The present invention relates to a solid cosmetic product, a process for producing said product, and a product prepared by the method.

BACKGROUND TO THE INVENTION

The present invention relates to products particularly those for use in contact with the human body.

A cosmetic product which has been increasingly popular is massage bars. These products contain a solidified oil or fat moulded into a product which may be held easily in the hand. Alternatively a larger sized product may be made from which a small piece may be broken and then used. In use, the massage bar is applied to the skin of the recipient either as a complete bar or by breaking off a small piece of product which is then applied to the skin. These solid products are both popular for home use and for application by a professional masseur.

For home use a single solid product which may be applied many times is often considered to be acceptable. However for professional use, for example by a masseur or in a spa, multiple use of a single product is not acceptable. For reasons of hygiene it is not acceptable for one product to be used on one recipient and then later used on a different recipient. This problem may be addressed by use of small pieces of product broken from a larger piece or by providing as small single use size samples. However small pieces often do not provide the same physical sensation to the recipient as being massaged with a larger bar of product. Furthermore if sections are broken from a larger product and used for massage, the broken sections may have rough or sharper edges leading to a less pleasant massage.

The present invention seeks to provide a solid cosmetic product which may be used as a massage bar and which allows for an enlarged bar while avoiding unnecessary waste of the product.

SUMMARY OF THE INVENTION

In a first aspect, there is provided a solid cosmetic composition comprising a vegetable butter wherein the solid composition has dispersed therein gas bubbles, and wherein the gas bubbles form from 5 to 19% of the volume of the solid cosmetic composition.

In a second aspect, there is provided a process for the production of a solid composition solid cosmetic composition comprising a vegetable butter wherein the solid composition has dispersed therein gas bubbles, and wherein the gas bubbles form from 5 to 19% of the volume of the solid cosmetic composition;
the process comprising the steps of:
i) melting one or more vegetable butters;
ii) agitating the melted butter such that gas bubbles are formed within the melted one or more vegetable butters; and
iii) allowing the mixture of step ii) to solidify.

In a third aspect, there is provided a process for the production of a solid composition solid cosmetic composition comprising a vegetable butter wherein the solid composition has dispersed therein gas bubbles, and wherein the gas bubbles form at least 5% of the volume of the solid cosmetic composition;
the process comprising the steps of:
i) melting one or more vegetable butters;
ii) agitating the melted butter such that gas bubbles are formed within the melted one or more vegetable butters; and
iii) allowing the mixture of step ii) to solidify.

In a fourth aspect, there is provided a product obtained or obtainable by a process for the production of a solid composition solid cosmetic composition comprising a vegetable butter wherein the solid composition has dispersed therein gas bubbles, and wherein the gas bubbles form from 5 to 19% of the volume of the solid cosmetic composition;
the process comprising the steps of:
i) melting one or more vegetable butters;
ii) agitating the melted butter such that gas bubbles are formed within the melted one or more vegetable butters; and
iii) allowing the mixture of step ii) to solidify.

In a fifth aspect, there is provided a product obtained or obtainable by a process for the production of a solid composition solid cosmetic composition comprising a vegetable butter wherein the solid composition has dispersed therein gas bubbles, and wherein the gas bubbles form at least 5% of the volume of the solid cosmetic composition;
the process comprising the steps of:
i) melting one or more vegetable butters;
ii) agitating the melted butter such that gas bubbles are formed within the melted one or more vegetable butters; and
iii) allowing the mixture of step ii) to solidify.

For ease of reference, these and further aspects of the present invention are now discussed under appropriate section headings. However, the teachings under each section are not necessarily limited to each particular section.

Advantages

By forming a cosmetic solid product which has gas bubbles entrapped therein, an aerated solid product is provided. The aerated product has a lower density than the non aerated product. In other words for a given volume a cosmetic product is provided have less mass or in other words containing less cosmetic material. Thus the present invention allows the user to have a hold a product which is of a suitable size and which also offers an enjoyable massage, while containing less cosmetic ingredient thereby minimising waste on disposal or allowing application of all of the product when providing a single massage to individual. It has also been found that products containing gas bubbles incorporated in an amount of 5 to 19% by volume provide a smoother feeling on the skin when applied.

DETAILED DESCRIPTION

Composition
As discussed herein, in one aspect of the present invention, there is provided a solid cosmetic composition comprising a vegetable butter wherein the solid composition has dispersed therein gas bubbles, and wherein the gas bubbles form from 5 to 19% of the volume of the solid cosmetic composition.

It will be understood by one skilled in the art that the nature of a cosmetic product means that the product is not edible. Thus in a further aspect the present invention provides a non-edible solid cosmetic composition comprising a vegetable butter wherein the solid composition has dispersed therein gas bubbles, and wherein the gas bubbles form from 5 to 19% of the volume of the solid cosmetic composition.

The solid products of the present invention are compositions which can substantially sustain their physical shape when unsupported by external means, e.g. packaging etc. Thus, they are considered to be solid, solid like, in solid form or in solid-like form at room temperature. For the avoidance of doubt the solid product must remain substantially solid at up to 30° C.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

Due to the solid form of the compositions of the present invention, external packaging is not required to maintain the shape of the composition.

The vegetable butter is a triglyceride which is found to be solid (including solid like, discussed above) at normal usage temperatures. For the avoidance of doubt the vegetable butter is a triglyceride which remains substantially solid at up to 30° C. It will be appreciated however that it is not a requirement that the vegetable butter have a solid fat content of 100% at normal usage temperatures. In a preferred aspect the solid fat has a solid fat content of at least 70%, preferably at least 80%, preferably at least 90%, preferably at least 95%, preferably at least 98%, preferably at least 99% at 25° C.

As discussed herein, in one aspect the present invention provides a process for the production of a solid composition solid cosmetic composition comprising a vegetable butter wherein the solid composition has dispersed therein gas bubbles, and wherein the gas bubbles form at least 5% of the volume of the solid cosmetic composition; the process comprising the steps of: i) melting one or more vegetable butters; ii) agitating the melted butter such that gas bubbles are formed within the melted one or more vegetable butters; and iii) allowing the mixture of step ii) to solidify. In one preferred aspect the gas bubbles form from 5 to 60% of the volume of the solid cosmetic composition. In one preferred aspect the gas bubbles form from 5 to 50% of the volume of the solid cosmetic composition. In one preferred aspect the gas bubbles form from 10 to 60% of the volume of the solid cosmetic composition. In a further preferred aspect the gas bubbles form from 10 to 50% of the volume of the solid cosmetic composition. In one preferred aspect the gas bubbles form from 15% to 60% of the volume of the solid cosmetic composition. In one preferred aspect the gas bubbles form from 15% to 50% of the volume of the solid cosmetic composition.

As discussed herein the gas bubbles which are incorporated into the solid product and entrapped by the solid product form from 5 to 19% of the volume of the solid cosmetic composition. In one preferred aspect the gas bubbles form from 5 to 18% of the volume of the solid cosmetic composition. In one preferred aspect the gas bubbles form from 5 to 17% of the volume of the solid cosmetic composition. In one preferred aspect the gas bubbles form from 10 to 19% of the volume of the solid cosmetic composition. In a further preferred aspect the gas bubbles form from 10 to 18% of the volume of the solid cosmetic composition. In one preferred aspect the gas bubbles form from 10% to 17% of the volume of the solid cosmetic composition.

The gas bubbles may be of any suitable gas. In one aspect the gas bubbles are of a gas selected from air, nitrogen, nitrous oxide, carbon dioxide and mixtures thereof.

The present invention provides a cosmetic product which is solid. The vegetable butters incorporated into the solid product are typically used as agents in massage. However the solid cosmetic product of the present invention may be used in any manner in which the end user sees fit. For example, the cosmetic product may be used in one or more of the following applications: tooth preparations, lip balms, solid bath salts, moisturisers, skincare, body lotions, shampoos, solid conditioners, hair dressings, face masks, bath melts, bath oils, shower gels, shower jellies, solid fragrance, solid henna hair dyes, shaving preparations, deodorants and bubble baths. However, in a preferred aspect the solid cosmetic composition of the present invention is a massage bar.

The composition of the present invention is typically made by moulding of an aerated product. Thus in one aspect the product of the present invention is prepared by melting and then aerating the ingredients of the product, placing the melted aerated product into a mould and allowing the aerated product to set. The aerated product is then released from the mould once solid. This process is described in further detail herein. It has been found that when an aerated product is formed in a mould it may be difficult to remove the aerated product from the mould because of the multiple points of contact between the aerated structure and the mould itself. To alleviate these problems of mould release it is desirable to coat the inside of the mould with a small amount of shell material and then form within this the solidified aerated product. Thus in a further preferred aspect the composition of the present invention comprises a shell coating. This shell coating is typically made from the same composition as the aerated product but which has not been aerated itself. Thus in a preferred aspect the shell coating is formed from the same material as the solid composition having dispersed therein gas bubbles. from the same composition as the aerated product. In one aspect the shell is made from a different composition to the aerated product. In one aspect the shell is made from at least the same ingredients as the aerated part of the product but in different amounts or in the absence of optional ingredients present in the aerated part of the product. Thus in a further aspect there is provided a solid cosmetic product comprising (a) a core material comprising a vegetable butter wherein the core material has dispersed therein gas bubbles, (b) a shell material comprising a vegetable butter, wherein the shell material at least partially encases the core material wherein the gas bubbles form from 5 to 19% of the volume of the solid cosmetic composition.

Vegetable Butter

The solid cosmetic product of the present invention must contain at least one vegetable butter. The term vegetable butter is understood by one skilled in the art and means a triglyceride obtainable from vegetable source which has the consistency of a butter. Vegetable butters include Aloe butter, Avocado butter, Cocoa butter, Coffee Bean butter, Cupuacu butter, Refined butter, Hemp Seed butter, Illipe butter, Kokum butter, Macadamia Nut butter, Mango butter, Mochacchino butter, Murumuru butter, Olive butter, Pistachio Nut butter, Shea butter, coconut butter, Shealoe butter and Sweet Almond butter. In a preferred aspect the vegetable butter is selected from Murumuru butter, Illipe butter, Mango butter, Avocado butter, Cupuacu butter, Coconut butter, Cocoa butter, Shea butter and mixtures thereof. In a preferred aspect the vegetable butter is selected from Cocoa butter, Shea butter and mixtures thereof.

Preferably the vegetable butter is a mixture of two or more vegetable butters. In a highly preferred aspect the vegetable butter is a mixture of cocoa butter and shea butter.

The mixture of two or more vegetable butters is preferably a mixture of a "hard" vegetable butter and a "soft" vegetable butter. It is understood by one skilled in the art that a hard vegetable butter is one containing a high saturated fat content and which therefore has a high solid fat content at room temperature. It is understood by one skilled in the art that a soft vegetable butter is one containing a high unsaturated fat content in which therefore has a low solid fat content at room temperature.

Preferred hard vegetable butters for use in accordance with the present invention may be selected from Cocoa butter, Illipe butter, Murumuru butter, Kokum butter and mixtures thereof.

Preferred soft vegetable butters for use in accordance with the present invention may be selected from Aloe butter, Avocado butter, Cupuacu butter, Macadamia Nut butter, Mango butter, Olive butter, Shea butter, Coconut butter, Pumpkin Seed butter, Peanut butter, Almond butter and mixtures thereof.

In one preferred aspect the vegetable butter is a mixture of (a) from 5 to 95 wt % of a first butter selected from Cocoa butter, Illipe butter, Murumuru butter, Kokum butter and mixtures thereof; and (b) from 5 to 95 wt % of a second butter selected from Aloe butter, Avocado butter, Cupuacu butter, Macadamia Nut butter, Mango butter, Olive butter, Shea butter, Coconut butter, Pumpkin Seed butter, Peanut butter, Almond butter and mixtures thereof.

The vegetable butter may be present in any amount to provide the desired physical characteristics of the solid cosmetic product. Preferably the vegetable butter is present in an amount of from about 10% to about 99% by weight of the total composition. Preferably the vegetable butter is present in an amount of from about 20% to about 99% by weight of the total composition. Preferably the vegetable butter is present in an amount of from about 30% to about 99% by weight of the total composition. Preferably the vegetable butter is present in an amount of from about 40% to about 99% by weight of the total composition. Preferably the vegetable butter is present in an amount of from about 50% to about 99% by weight of the total composition. Preferably the vegetable butter is present in an amount of from about 60% to about 99% by weight of the total composition. Preferably the vegetable butter is present in an amount of from about 70% to about 99% by weight of the total composition. Preferably the vegetable butter is present in an amount of from about 80% to about 99% by weight of the total composition. Preferably the vegetable butter is present in an amount of from about 85% to about 99% by weight of the total composition. Preferably the vegetable butter is present in an amount of from about 90% to about 99% by weight of the total composition. Preferably the vegetable butter is present in an amount of from about 95% to about 99% by weight of the total composition. Preferably the vegetable butter is present in an amount of approximately 97% by weight of the total composition.

When the solid cosmetic product contains cocoa butter, the cocoa butter may be present in any suitable amount. Typically the cocoa butter is present in an amount of from about 5% to about 94% by weight of the total composition. Preferably the cocoa butter is present in an amount of from about 10% to about 94% by weight of the total composition. Preferably the cocoa butter is present in an amount of from about 20% to about 94% by weight of the total composition. Preferably the cocoa butter is present in an amount of from about 30% to about 94% by weight of the total composition. Preferably the cocoa butter is present in an amount of from about 40% to about 94% by weight of the total composition. Preferably the cocoa butter is present in an amount of from about 50% to about 94% by weight of the total composition. Preferably the cocoa butter is present in an amount of from about 60% to about 94% by weight of the total composition. Preferably the cocoa butter is present in an amount of from about 60% to about 90% by weight of the total composition. Preferably the cocoa butter is present in an amount of from about 60% to about 85% by weight of the total composition. Preferably the cocoa butter is present in an amount of from about 65% to about 80% by weight of the total composition. Preferably the cocoa butter is present in an amount of from about 70% to about 80% by weight of the total composition. Preferably the cocoa butter is present in an amount of approximately 70% by weight of the total composition.

When the solid cosmetic product contains shea butter, the shea butter may be present in any suitable amount. Typically the shea butter is present in an amount of from about 5% to about 94% by weight of the total composition. Preferably the shea butter is present in an amount of from about 5% to about 90% by weight of the total composition. Preferably the shea butter is present in an amount of from about 5% to about 80% by weight of the total composition. Preferably the shea butter is present in an amount of from about 5% to about 70% by weight of the total composition. Preferably the shea butter is present in an amount of from about 5% to about 60% by weight of the total composition. Preferably the shea butter is present in an amount of from about 5% to about 50% by weight of the total composition. Preferably the shea butter is present in an amount of from about 5% to about 40% by weight of the total composition. Preferably the shea butter is present in an amount of from about 5% to about 30% by weight of the total composition. Preferably the shea butter is present in an amount of from about 10% to about 30% by weight of the total composition. Preferably the shea butter is present in an amount of from about 15% to about 30% by weight of the total composition. Preferably the shea butter is present in an amount of from about 20% to about 30% by weight of the total composition. Preferably the shea butter is present in an amount of approximately 26% by weight of the total composition.

Additional Components

The solid product of the present invention may also comprise one or more cosmetically acceptable additives. The person skilled in the art is aware of a range of cosmetically acceptable additives which are suitable for incorporation into such compositions. For example, binders, fillers, opacifiers, perfumes, fragrances, decorative items and mixtures thereof.

It is particularly preferred that the composition of the present invention further comprises a fragrance. Preferably the fragrance is selected from essential oils. Preferably the fragrance, and more preferably the essential oil, is present in an amount of from about 0.5% to about 4% by weight of the total composition. More preferred amounts are from about 0.5% to about 3.5% by weight of the total composition, such as from about 0.5% to about 3% by weight of the total composition, such as from about 1% to about 3% by weight of the total composition, such as from about 1.5% to about 2.5% by weight of the total composition, such as approximately 2% by weight of the total composition.

Fruit and herb extracts and juices, vegetable oils and essential oils are all compatible with the composition. Colours, both naturally derived and synthetic can be used to colour the product.

In one embodiment, the cosmetically acceptable additives are selected from the group consisting of essential oils, vitamins, fragrances, colourings, clays, decorative articles and mixtures thereof.

The essential oils may be selected based on the fragrance desired, skin type to be treated and other effects desired based on the well known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the solid product are selected from Tarragon, Lemon myrtle, Jasmin, Ylang ylang, Labdunum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, Litsea Cubeba, Cardamon, Tonka, and Chamomile blue. In one embodiment, the one or more essential oils present in the solid product are selected from Tarragon, Lemon myrtle, Labdunum, and Lemon.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the solid product of a material, such as a natural material, that has a high vitamin content.

The ingredients in the present invention do not require cosmetic preservatives. The use of cosmetic preservatives can increase the potential to irritate the skin.

The decorative items which may be present in the solid product include items such as glitter, paper such as rice paper, sequins, dried or fresh flowers, herbs, vegetables, parts thereof or mixtures thereof. Other enhancing materials may also be incorporated Further preferred additive materials include vegetable oils, chocolate, herbs and spices, cosmetic colours (e.g. paprika, gardenia extract, dmc red no. 30), beans (e.g. aduki), fruit, fresh or dried (e.g. banana, avocado, mango, papaya, kiwi, raspberry, strawberry, blueberries, grapes, tomato, asparagus, or cucumber), honey, glycerin, cosmetic glitter, other vegetable butters (e.g. mango, avocado), clays (e.g. kaolin), starches (e.g. corn starch) and mixtures thereof.

The above ranges provide preferred amounts of each of the components. Each of these ranges may be taken alone or combined with one or more other component ranges to provide a preferred aspect of the invention.

One highly preferred composition accordance with the present invention comprises
(i) cocoa butter in an amount of from about 60% to about 80% by weight of the total composition
(ii) shea butter in an amount of from about 15% to about 35% by weight of the total composition
(iii) fragrance in an amount of from about 2% to about 4% by weight of the total composition.

Process

As discussed herein, the invention provides a process for the production of a solid composition solid cosmetic composition comprising a vegetable butter wherein the solid composition has dispersed therein gas bubbles, and wherein the gas bubbles form at least 5% of the volume of the solid cosmetic composition;
 the process comprising the steps of:
  i) melting one or more vegetable butters;
  ii) agitating the melted butter such that gas bubbles are formed within the melted one or more vegetable butters; and
  iii) allowing the mixture of step ii) to solidify.

The present invention further provides a process for the production of a solid cosmetic composition comprising a vegetable butter wherein the solid composition has dispersed therein gas bubbles, and wherein the gas bubbles form from 5 to 19% of the volume of the solid cosmetic composition;
 the process comprising the steps of:
  i) melting one or more vegetable butters;
  ii) agitating the melted butter such that gas bubbles are formed within the melted one or more vegetable butters; and
  iii) allowing the mixture of step ii) to solidify.

It will be understood by one skilled in the art that step (ii) of the present invention, in which the melted butter is agitated such that gas bubbles are formed within the melted one or more vegetable butters, may be performed by any suitable agitation. The agitation can be mixing, such as high-speed or high shear mixing and is preferably achieved by whisking.

Whisking is the preferred method of agitating the one or more vegetable butters. The one or more vegetable butters can be agitated, for example whisked, at any suitable temperature such that they are melted and allow for agitation such that gas bubbles are incorporated. A preferred temperature is from 22 to 35° C. A highly preferred temperature is 28° C. If agitation is achieved through use of a whisk this can be either a hand whisk, an electric hand whisk or industrial Hobart mixer with a whisk attachment.

Once gas bubbles have been incorporated into the melted one or more vegetable butters, preferably steps are taken to maintain the bubbles within the one or more vegetable butters during solidification. Preferably this is achieved by placing the solidifying product in an atmosphere having a pressure of greater than one bar. Preferably the gas used to provide an atmosphere having greater than one bar is a cooled gas. Preferred gases are nitrous oxide, carbon dioxide and air.

In a further aspect it is advantageous to solidify the product in an atmosphere having a constant pressure. This constant pressure need not be greater than atmospheric pressure. In one aspect the constant pressure is less than atmospheric pressure. Preferably the product is solidified at a pressure of from 0.2 to 1.0 bar. Preferably the product is solidified at a pressure of 0.6 bar. The solidifying product is ideally held at a constant pressure, for example at a pressure of from 0.2 to 1.0 bar such as 0.6 bar for 2-15 seconds with the best results being achieved after 7 seconds.

A typical process for preparing a product in accordance with the present invention is as follows:
 1. Providing one or more vegetable butters and heating the one or more butters to a temperatures of 50-70° C.
 2. Cooling the one or more butters such that the butters solidify. Typically they are cooled to temperatures of 22-32° C., with particularly advantageous results being achieved at 27° C. Without being bound by theory, it is understood that this heating and cooling step result in the formation of a specific crystalline structure of the butter, such as cocoa butter. This specific crystalline form is known as Form V and provides a butter that once solidified readily melts at body temperature, 3. The butters may then be reheated to a temperature of 33-45° C. to prevent the formation of alternative crystalline structures which have lower melting temperatures and cause the solid cosmetic composition to melt at temperatures lower than body temperature. This also believed to slow down the crystal growth so that a structure that forms is not too solid, i.e. the inhibition of adverse crystal growth prevents the preparation of a product that will not melt on skin contact.

4. The fragrance materials can then be added and gently mixed as not to disrupt the crystal formation.

5. Once the product has cooled to below 32° C. it can be treated as follows:

a. Prior to physical agitation (i.e. whisking) the composition is cooled to 22-32° C., with particularly advantageous results achieved at 27° C., then whisked for 2 minutes to 1 hour.

b. The composition is then left to stand for 30 seconds-2 minutes. This allows for larger gas bubbles to escape and permits the production of composition that is smooth and has a solid appearance.

c. The butters can then be poured into moulds and left to completely solidify, at temperatures between 20-32° C.

A further typical process for preparing a product in accordance with the present invention is as follows. The butter mix is melted, cooled and heated again (tempered) the manner as described herein. Once the butters reach 24° C., a shearing force is applied (i.e. the mixture is whisked) on a medium-high power for 5 minutes or until resistance is felt during the whisking process. The medium-high power provides enough energy to the system to incorporate air into the system during the formation of crystals. However, because a medium high power is used, the energy generated is not sufficient enough to significantly hamper the cooling process. Thus crystals to are allowed to aggregate (join together). She mix may then be left to stand for 1 minute, this allows a crystalline system to fully form and for crystals to start to cluster—at this point the butter mix will become stiff. The butter mix should then be sheared (i.e. whisked) for an additional 5 minutes. This energy separates pushes the crystals back into their individual form, allowing the butter mix to be poured into the moulds. Once into the moulds the crystals will once again form clusters, then solidify into the butter network. The molecular dynamic composition of butter is discussed in this reference Campos et al. 2010 in Crystal Growth & Design (American Society Of Chemistry), Vol. 10, No. 1 Pg 207-217.

In one aspect the moulds are pre-cooled before pouring to ensure that after solidification of the product, the product can be released from the mould. Furthermore, once the bars have loosely set, the moulds may be turned as this is found to assist in removing the products from the mould.

The shape of the solid products of the present invention is not limited. It may be that the solid products are provided with a shape which would be aesthetically pleasing and/or which aids in the use of the product. For example, it may be that the solid product is produced in such a manner so that it solidifies in a shape which is ergonomically acceptable to the user. Therefore, in one embodiment of the process of the present invention, the mixture of step i) and/or step ii) is pressed into a mould, allowed to solidify, and then turned out to produce the solid product.

As described herein, the solid product may further comprise one or more cosmetically acceptable additives. In one embodiment, the process further comprises the step of combining with the mixture of step i) and/or step ii) one or more cosmetically acceptable additives as defined herein and/or the dispersant defined herein.

The present invention also provides a product obtained or obtainable by a process for the production of a solid composition solid cosmetic composition comprising a vegetable butter wherein the solid composition has dispersed therein gas bubbles, and wherein the gas bubbles form from 5 to 19% of the volume of the solid cosmetic composition;

the process comprising the steps of:
i) melting one or more vegetable butters;
ii) agitating the melted butter such that gas bubbles are formed within the melted one or more vegetable butters; and
iii) allowing the mixture of step ii) to solidify.

Method

In one aspect of the present invention, there is provided a method comprising contacting the skin of a user with water in which the solid product as defined herein has dissolved or in which the solid product as defined herein is dissolving. In a typical method water in run in to the bath at acceptable temperature. The user immerses their body in the water and the solid product is dropped in to the water. The user then watches the effect of the product on the surface of the water or as it effervesces beneath the surface. The user then bathes in the water.

Example

The invention will now be described with reference to the following non-limiting example.

A general methodology for preparing compositions in accordance with the present invention is as follows:

1. Warm the one or more vegetable butters to 50-70° C. to melt.
2. Cool the butter mix down to 22-32° C., then re-heat to 33-45° C.
3. Cool the butter mix down to 22-32° C., and add any additional components, such as decorative materials, fragrances and colourings.
4. Whisk the mixture on low-high speed, for 2 minutes-1 hour.
5. Pour the whisked mixture into moulds, and then cool to 0-20° C. to set.

A solid product having the following composition was prepared.

| Formula % | Raw Material Type | Grams |
| --- | --- | --- |
| 70.50 | Cocoa butter | 70.500 |
| 26.50 | Shea butter | 26.500 |
| 3.00 | Fragrance | 3.000 |
| 100.00 | | 100.0 |

The product was prepared as follows:
1. the two vegetable butters were combined and heated to 60° C. to melt
2. the butter mix was cooled to 25° C. or 27° C., then reheated to 35° C.
3. mixture was then cooled to 25° C. or 27° C. and the fragrance added
4. the mixture was whisked on a medium speed for 6, 9 or 12 minutes
5. the whisked mixture was poured into moulds and then cooled at 8° C. to set The following samples were prepared. The temperature variations of steps 2 and 3 above are stated together with the duration of whisking.

| Sample No. | Temperature Flux A | Temperature Flux B | Temperature Flu C | Duration Of Whisk |
|---|---|---|---|---|
| 1 | Cooled to 27° C. | Warmed to 35° C. | Cooled to 27° C. | 6 minutes |
| 2 | Cooled to 27° C. | Warmed to 35° C. | Cooled to 27° C. | 9 minutes |
| 3 | Cooled to 27° C. | Warmed to 35° C. | Cooled to 27° C. | 12 minutes |
| 4 | Cooled to 25° C. | Warmed to 35° C. | Cooled to 25° C. | 3 minutes |
| 5 | Cooled to 25° C. | Warmed to 35° C. | Cooled to 25° C. | 6 minutes |
| 6 | Cooled to 25° C. | Warmed to 35° C. | Cooled to 25° C. | 9 minutes |

The mixtures of poured into a standard size mould and allowed to set. Multiple runs of each sample were prepared. The average mass of the sample was calculated and compared against the average mass of a non-aerated sample. From this the volume of the aerated samples occupied by gas was calculated.

| | Standard Weight (Grams) | Sample No. 1 Weight (Grams) | Sample No. 2 Weight (Grams) | Sample No. 3 Weight (Grams) | Sample No. 4 Weight (Grams) | Sample No. 5 Weight (Grams) | Sample No. 6 Weight (Grams) |
|---|---|---|---|---|---|---|---|
| Average Mass | 114.58 | 109.43 | 110.54 | 73.07 | 95.99 | 95.97 | 61.72 |
| % Gas (Fixed volume) | 0% | 5.50% | 3.52% | 36.22% | 16.22% | 16.24% | 46.13% |

It was found that sample number 2 which had a relatively low degree of aeration i.e. the proportion of the volume which was formed of gas bubbles was less than 5%, was effectively equivalent to the control sample. In contrast sample number 1 which had approximately 5% gas bubbles was found to have a smoother application feel when compared to the control product. This was further enhanced in respect of samples 4 and 5. Samples 3 and 6 which contained a high proportion of gas bubbles (36.22% and 46.13%) were effective in providing products which were easy to handle but contained considerably less vegetable butter than the control product of the same volume. This was useful in minimizing wastage in single use applications and also provided a product which felt "lighter" in the hand.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A solid cosmetic composition comprising:
a vegetable butter wherein the solid cosmetic composition has dispersed therein gas bubbles, wherein the gas bubbles form from 5 to 19% of the volume of the solid cosmetic composition; wherein the vegetable butter is present in an amount of 60-99% by weight of the total composition; wherein the composition comprises a shell coating; wherein the solid cosmetic composition is a solid non-edible cosmetic composition having a physical shape and the solid non-edible cosmetic composition substantially sustains the physical shape when unsupported externally, and wherein the solid non-edible cosmetic composition is solid at room temperature and remains substantially solid at up to a temperature of 30° C.

2. A solid composition according to claim 1, wherein the vegetable butter is a mixture of two or more vegetable butters.

3. A solid composition according to claim 1, wherein the vegetable butter is selected from aloe butter, avocado butter, cocoa butter, coffee bean butter, cupuacu butter, refined butter, hemp seed butter, illipe butter, kokum butter, macadamia nut butter, mango butter, mochacchino butter, murumuru butter, olive butter, pistachio nut butter, shea butter, coconut butter, shealoe butter, sweet almond butter and mixtures thereof.

4. A solid composition according to claim 3, wherein the vegetable butter is a mixture of cocoa butter and shea butter.

5. A solid composition according to claim 1, wherein the vegetable butter is present in an amount of from about 80% to about 99% by weight of the total composition.

6. A solid composition according to claim 1, comprising cocoa butter in an amount of from about 5% to about 94% by weight of the total composition.

7. A solid composition according to claim 6, comprising cocoa butter in an amount of from about 60% to about 80% by weight of the total composition.

8. A solid composition according to claim 1, comprising shea butter in an amount of from about 5% to about 94% by weight of the total composition.

9. A solid composition according to claim 8, comprising shea butter in an amount of from about 15% to about 35% by weight of the total composition.

10. A solid composition according to claim 1, further comprising a fragrance.

11. A solid composition according to claim 10, wherein the fragrance is selected from essential oils.

12. A solid composition according to claim 10, comprising the fragrance in an amount of from about 0.5% to about 4% by weight of the total composition.

13. A solid composition according to claim 1, comprising
   (i) cocoa butter in an amount of from about 60% to about 80% by weight of the total composition
   (ii) shea butter in an amount of from about 15% to about 35% by weight of the total composition
   (iii) fragrance in an amount of from about 2% to about 4% by weight of the total composition.

14. A solid composition according to claim 1, further comprising at least one additional component selected from binders, fillers, opacifiers, perfumes, fragrances, decorative items and mixtures thereof.

15. A solid composition according to claim 1, wherein the composition is a massage bar.

16. A solid composition according to claim 1, wherein the shell coating is formed from the same material as the solid composition having dispersed therein gas bubbles.

17. A cosmetic method comprising contacting the skin of a user with a solid cosmetic composition as defined in claim 1.

* * * * *